US008863855B2

(12) United States Patent
Kotlar

(10) Patent No.: US 8,863,855 B2
(45) Date of Patent: Oct. 21, 2014

(54) METHOD OF ENHANCING OIL RECOVERY

(75) Inventor: Hans Kristian Kotlar, Stavanger (NO)

(73) Assignee: Statoil ASA, Stavanger (NO)

( * ) Notice: Subject to any disclaimer, the term of this patent is extended or adjusted under 35 U.S.C. 154(b) by 328 days.

(21) Appl. No.: 12/452,259

(22) PCT Filed: Jun. 26, 2008

(86) PCT No.: PCT/GB2008/002209
§ 371 (c)(1),
(2), (4) Date: Mar. 19, 2010

(87) PCT Pub. No.: WO2009/001098
PCT Pub. Date: Dec. 31, 2008

(65) Prior Publication Data
US 2010/0163230 A1     Jul. 1, 2010

(30) Foreign Application Priority Data

Jun. 26, 2007 (GB) .................................. 0712395.3

(51) Int. Cl.
E21B 43/22 (2006.01)
E21B 43/24 (2006.01)
E21B 43/16 (2006.01)
C12N 1/26 (2006.01)
C12N 1/20 (2006.01)
C12P 39/00 (2006.01)
C09K 8/592 (2006.01)
C09K 8/582 (2006.01)

(52) U.S. Cl.
CPC . *C09K 8/582* (2013.01); *C12N 1/26* (2013.01); *C12N 1/20* (2013.01); *C12P 39/00* (2013.01); *C09K 8/592* (2013.01)
USPC ........................ 166/402; 166/246; 166/272.1

(58) Field of Classification Search
None
See application file for complete search history.

(56) References Cited

U.S. PATENT DOCUMENTS

| 2,633,919 | A |   | 4/1953  | Bauer et al. |         |
|-----------|---|---|---------|--------------|---------|
| 2,832,754 | A |   | 4/1958  | Jex et al.   |         |
| 2,935,475 | A |   | 5/1960  | Bernard      |         |
| 2,939,839 | A |   | 6/1960  | Brukner      |         |
| 2,975,835 | A |   | 3/1961  | Bond         |         |
| 3,185,216 | A | * | 5/1965  | Hitzman      | 166/246 |
| 3,199,587 | A | * | 8/1965  | Santourian   | 166/245 |
| 3,199,590 | A |   | 8/1965  | Young        |         |
| 3,250,330 | A |   | 5/1966  | Smith, Jr.   |         |
| 3,286,770 | A |   | 11/1966 | Knox et al.  |         |
| 3,294,166 | A |   | 12/1966 | Havenaar et al. |      |
| 3,364,994 | A |   | 1/1968  | Sterrett     |         |
| 3,552,493 | A |   | 1/1971  | Bezemer      |         |
| 3,615,794 | A |   | 10/1971 | Nimerick     |         |
| 3,625,287 | A |   | 12/1971 | Young        |         |
| 4,074,536 | A |   | 2/1978  | Young        |         |
| 4,120,842 | A |   | 10/1978 | Harnsberger  |         |
| 4,384,044 | A |   | 5/1983  | Kim et al.   |         |
| 4,417,623 | A |   | 11/1983 | Anthony      |         |
| 4,450,908 | A |   | 5/1984  | Hitzman      | 166/246 |
| 4,479,543 | A |   | 10/1984 | Kalfayan et al. |      |
| 4,498,538 | A |   | 2/1985  | Watkins et al. |       |
| 4,506,044 | A |   | 3/1985  | Cox et al.   |         |
| 4,530,956 | A |   | 7/1985  | Ugelstad et al. |      |
| 4,549,609 | A |   | 10/1985 | Watkins et al. |       |
| 4,580,633 | A |   | 4/1986  | Watkins et al. |       |
| 4,646,835 | A |   | 3/1987  | Watkins et al. |       |
| 4,660,642 | A |   | 4/1987  | Young        |         |
| 4,678,033 | A | * | 7/1987  | Killough     | 166/246 |
| 4,689,085 | A |   | 8/1987  | Plueddemann  |         |
| 4,708,207 | A |   | 11/1987 | Kalfayan et al. |      |
| 4,743,545 | A |   | 5/1988  | Torobin      |         |
| 4,787,453 | A |   | 11/1988 | Hewgill et al. |       |
| 4,846,981 | A |   | 7/1989  | Brost        |         |
| 4,850,745 | A |   | 7/1989  | Hater et al. |         |
| 4,905,761 | A | * | 3/1990  | Bryant       | 166/246 |
| 4,938,287 | A |   | 7/1990  | Friedman et al. |      |
| 5,043,364 | A |   | 8/1991  | Moradi-Araghi et al. | |
| 5,083,611 | A |   | 1/1992  | Clark et al. |         |
| 5,129,458 | A |   | 7/1992  | King et al.  |         |
| 5,163,510 | A | * | 11/1992 | Sunde        | 166/246 |
| 5,169,561 | A |   | 12/1992 | Gentle et al. |        |
| 5,250,201 | A |   | 10/1993 | Shilo et al. |         |
| 5,297,625 | A |   | 3/1994  | Premuzic et al. |      |
| 5,337,820 | A |   | 8/1994  | Jenneman et al. |      |
| 5,376,183 | A |   | 12/1994 | Gatt et al.  |         |
| 5,379,841 | A |   | 1/1995  | Pusch et al. |         |
| 5,492,828 | A |   | 2/1996  | Premuzic et al. | 435/245 |
| 5,530,095 | A |   | 6/1996  | Vaughn et al. |        |
| 5,701,956 | A |   | 12/1997 | Hardy et al. |         |
| 5,735,349 | A |   | 4/1998  | Dawson et al. |        |

(Continued)

FOREIGN PATENT DOCUMENTS

| CN | 1420254 | 5/2003 |
| CN | 1472157 | 2/2004 |

(Continued)

OTHER PUBLICATIONS

"What are oil sands and heavy oil?" Retrieved Oct. 28, 2011 from http://www.centreforenergy.com/AboutEnergy/ONG/OilsandsHeavyOil/Overview.asp.*

Response after Non-Final Action filed Jul. 18, 2011 in U.S. Appl. No. 11/919,367, filed Apr. 26, 2006 (Inventors: Godoy et al.).

Non-Final Action issued Feb. 16, 2011 in U.S. Appl. No. 11/919,367, filed Apr. 26, 2006 (Inventors: Godoy et al.).

Response after Non-Final Action filed Nov. 29, 2010 in U.S. Appl. No. 11/919,367, filed Apr. 26, 2006 (Inventors: Godoy et al.).

(Continued)

*Primary Examiner* — Angela M DiTrani
(74) *Attorney, Agent, or Firm* — Ballard Spahr LLP

(57) ABSTRACT

Methods of enhancing oil recovery from subterranean hydrocarbon reservoirs are described, wherein a microorganism capable of digesting oil is injected into the formation.

28 Claims, 1 Drawing Sheet

(56) References Cited

U.S. PATENT DOCUMENTS

| | | | |
|---|---|---|---|
| 5,806,593 | A | 9/1998 | Surles |
| 6,024,791 | A | 2/2000 | Sonoda et al. |
| 6,169,058 | B1 | 1/2001 | Le et al. |
| 6,210,476 | B1 | 4/2001 | Chatterji et al. |
| 6,228,812 | B1 | 5/2001 | Dawson et al. |
| 6,401,819 | B1 | 6/2002 | Harris et al. |
| 6,474,413 | B1 | 11/2002 | Barbosa et al. |
| 6,476,169 | B1 | 11/2002 | Eoff et al. |
| 6,543,535 | B2 * | 4/2003 | Converse et al. ............ 166/246 |
| 6,702,044 | B2 | 3/2004 | Reddy et al. |
| 7,325,603 | B2 | 2/2008 | Kotlar |
| 7,922,893 | B2 * | 4/2011 | Busche et al. .................. 208/46 |
| 7,964,539 | B2 | 6/2011 | Kotlar ........................... 507/233 |
| 8,210,261 | B2 | 7/2012 | Godøy et al. ................. 166/292 |
| 2002/0104651 | A1 | 8/2002 | McClung |
| 2002/0123433 | A1 | 9/2002 | Goodhue, Jr. et al. |
| 2003/0131764 | A1 | 7/2003 | Lessard et al. |
| 2003/0216263 | A1 | 11/2003 | Tibbles et al. |
| 2004/0177957 | A1 | 9/2004 | Kalfayan et al. |
| 2005/0173116 | A1 | 8/2005 | Nguyen et al. |
| 2007/0158070 | A1 | 7/2007 | Endres et al. |

FOREIGN PATENT DOCUMENTS

| | | |
|---|---|---|
| EP | 0 003 905 | 9/1979 |
| EP | 0 224 346 | 3/1986 |
| EP | 0 187 092 | 7/1986 |
| EP | 0 193 369 | 9/1986 |
| EP | 0 265 563 | 10/1986 |
| EP | 0 266 043 | 4/1988 |
| EP | 0 365 390 | 4/1990 |
| EP | 0 656 459 | 6/1995 |
| EP | 0 692 464 | 1/1996 |
| EP | 1 235 974 | 1/2005 |
| GB | 1 021 528 | 3/1966 |
| GB | 1 022 742 | 3/1966 |
| GB | 1 511 589 | 5/1978 |
| GB | 2 222 420 | 3/1990 |
| GB | 2 290 096 | 12/1995 |
| GB | 2 377 930 | 1/2003 |
| GB | 2 387 613 | 10/2003 |
| GB | 2 399 364 | 9/2004 |
| GB | 2 425 531 | 11/2006 |
| JP | 72033048 | 1/1968 |
| KR | 20020044733 | 6/2002 |
| KR | 20030071279 | 9/2003 |
| SU | 1 025 868 | 6/1983 |
| SU | 1 661 379 | 7/1991 |
| WO | WO 88/00948 | 2/1988 |
| WO | WO 92/17413 | 10/1992 |
| WO | WO 96/27070 | 9/1996 |
| WO | WO 97/45625 | 12/1997 |
| WO | WO 98/27314 | 6/1998 |
| WO | WO 99/03666 | 1/1999 |
| WO | WO 99/19375 | 4/1999 |
| WO | WO 99/54592 | 10/1999 |
| WO | WO 01/34939 | 5/2001 |
| WO | WO 02/095187 | 11/2002 |
| WO | WO 03/010107 | 2/2003 |
| WO | WO 03/087010 | 10/2003 |
| WO | WO 2005/005773 | 1/2005 |
| WO | WO 2005/073278 | 2/2005 |
| WO | WO 2005/024175 | 3/2005 |
| WO | WO 2005/124099 | 12/2005 |
| WO | WO 2005/124100 | 12/2005 |
| WO | WO 2006/114623 | 11/2006 |
| WO | WO 2006/118467 | 11/2006 |
| WO | WO 2007/033489 | 3/2007 |
| WO | WO 2009/001098 | 12/2008 |
| WO | WO 2009/027680 | 3/2009 |

OTHER PUBLICATIONS

Non-Final Rejection issued May 27, 2010 in U.S. Appl. No. 11/919,367, filed Apr. 26, 2006 (Inventors: Godoy et al.).
Preliminary Amendment filed Oct. 25, 2007 in U.S. Appl. No. 11/919,367, filed Apr. 26, 2006 (Inventors: Godoy et al.).
Issue Notification issued Jan. 16, 2008 in U.S. Appl. No. 10/478,776, filed May 24, 2002 (Inventors: Kotlar et al.).
Supplemental Notice of Allowance issued Nov. 30, 2007 in U.S. Appl. No. 10/478,776, filed May 24, 2002 (Inventors: Kotlar et al.).
Notice of Allowance & Examiner Interview Summary issued Aug. 30, 2007 in U.S. Appl. No. 10/478,776, filed May 24, 2002 (Inventors: Kotlar et al.).
Response after Non-Final Office Action filed Jul. 10, 2007 in U.S. Appl. No. 10/478,776, filed May 21, 2002 (Inventors: Kotlar et al.).
Non-Final Rejection issued Jan. 12, 2007 in U.S. Appl. No. 10/478,776, filed May 21, 2002 (Inventors: Kotlar et al.).
Response after Final Office Action filed Dec. 22, 2006 in U.S. Appl. No. 10/478,776, filed May 21, 2002 (Inventors: Kotlar et al.).
Final Rejection issued Jun. 23, 2006 in U.S. Appl. No. 10/478,776, filed May 21, 2002 (Inventors: Kotlar et al.).
Response after Non-Final Office Action filed Mar. 27, 2006 in U.S. Appl. No. 10/478,776, filed May 21, 2002 (Inventors: Kotlar et al.).
Non-Final Rejection issued Sep. 27, 2005 in U.S. Appl. No. 10/478,776, filed May 21, 2002 (Inventors: Kotlar et al.).
Preliminary Amendment filed Nov. 21, 2003 in U.S. Appl. No. 10/478,776, filed May 21, 2002 (Inventors: Kotlar et al.).
Non-Final Office Action issued Aug. 9, 2011 in U.S. Appl. No. 11/629,729, filed Jun. 17, 2005 (Inventors: Kotlar et al.).
Response after Final Office Action filed May 27, 2010 in U.S. Appl. No. 11/629,729, filed Jun. 17, 2005 (Inventors: Kotlar et al.).
Final Office Action issued Jan. 27, 2010 in U.S. Appl. No. 11/629,729, filed Jun. 17, 2005 (Inventors: Kotlar et al.).
Response after Non-Final Office Action filed Nov. 12, 2009 in U.S. Appl. No. 11/629,729, filed Jun. 17, 2005 (Inventors: Kotlar et al.).
Non-Final Office Action issued May 12, 2009 in U.S. Appl. No. 11/629,729, filed Jun. 17, 2005 (Inventors: Kotlar et al.).
Response after Non-Final Office Action filed Jan. 9, 2009 in U.S. Appl. No. 11/629,729, filed Jun. 17, 2005 (Inventors: Kotlar et al.).
Non-Final Office Action issued Jul. 9, 2008 in U.S. Appl. No. 11/629,729, filed Jun. 17, 2005 (Inventors: Kotlar et al.).
Response to Restriction Requirement filed May 19, 2008 in U.S. Appl. No. 11/629,729, filed Jun. 17, 2005 (Inventors: Kotlar et al.).
Restriction Requirement issued Mar. 19, 2008 in U.S. Appl. No. 11/629,729, filed Jun. 17, 2005 (Inventors: Kotlar et al.).
Preliminary Amendment filed Dec. 5, 2006 in U.S. Appl. No. 11/629,729, filed Jun. 17, 2005 (Inventors: Kotlar et al.).
Issue Notification issued Jun. 1, 2011 in U.S. Appl. No. 11/629,636, filed Jun. 17, 2005 (Inventors: H.K. Kotlar).
Response to Rule 312 Communication issued May 12, 2011 in U.S. Appl. No. 11/629,636, filed Jun. 17, 2005 (Inventors: H.K. Kotlar).
Response to Notice to File Corrected Application Papers filed May 10, 2011 in U.S. Appl. No. 11/629,636, filed Jun. 17, 2005 (Inventors: H.K. Kotlar).
Notice to File Corrected Application Papers issued Mar. 24, 2011 in U.S. Appl. No. 11/629,636, filed Jun. 17, 2005 (Inventors: H.K. Kotlar).
Notice of Allowance issued Feb. 11, 2011 in U.S. Appl. No. 11/629,636, filed Jun. 17, 2005 (Inventors: H.K. Kotlar).
Summary of Examiner Interview issued Nov. 24, 2010 in U.S. Appl. No. 11/629,636, filed Jun. 17, 2005 (Inventors: H.K. Kotlar).
Response after Final Office Action filed Nov. 19, 2010 in U.S. Appl. No. 11/629,636, filed Jun. 17, 2005 (Inventors: H.K. Kotlar).
Final Office Action issued Jul. 23, 2010 in U.S. Appl. No. 11/629,636, filed Jun. 17, 2005 (Inventors: H.K. Kotlar).
Response after Non-Final Office Action filed Apr. 23, 2010 in U.S. Appl. No. 11/629,636, filed Jun. 17, 2005 (Inventors: H.K. Kotlar).
Non-Final Office Action issued Oct. 23, 2009 in U.S. Appl. No. 11/629,636, filed Jun. 17, 2005 (Inventors: H.K. Kotlar).
Response after Non-Final Office Action filed Jun. 23, 2009 in U.S. Appl. No. 11/629,636, filed Jun. 17, 2005 (Inventor: H.K. Kotlar).
Non-Final Office Action issued Dec. 23, 2008 in U.S. Appl. No. 11/629,636, filed Jun. 17, 2005 (Inventor: H.K. Kotlar).
Preliminary Amendment filed Dec. 15, 2006 in U.S. Appl. No. 11/629,636, filed Jun. 17, 2005 (Inventor: H.K. Kotlar).

(56) References Cited

OTHER PUBLICATIONS

Altschul SF, Madden TL, Schäffer AA, Zhang J, Zhang Z, Miller W, Lipman DJ. (1997) Gapped BLAST and PSI-BLAST: a new generation of protein database search programs. Nucleic Acids Res. 25(17): 3389-3402.
Anonymous. (1995) Method for the consolidation of incompetent formations. Kenneth Mason Publications Ltd., United Kingdom, ISSN 0374-4353.
Cannio et al. (1998) An autonomously replicating transforming vector for *Sulfolobus solfataricus*. J. Bacteriol., 180(12): 3237-3240.
Collins IR. Scale Inhibition by Poly(amino acids). Shared Petrotechnical Resource, Chertsey Road, Sunbury-on-Thames, Middlesex T16 7LN, pp. 1-22.
DeLong EF. (1992) Archaea in coastal marine environments. Proc Natl Acad Sci USA. 89(12):5685-5689.
Feitkenhauer H, Märkl H. (2003) Biodegradation of aliphatic and aromatic hydrocarbons at high temperatures. Water Sci Technol. 47(10): 123-130.
Fenn LB, Taylor RM, Matocha JE. (1981) Ammonia Losses from Surface-Applied Nitrogen Fertilizer as Controlled by Soluble Calcium and Magnesium: General Theory 1. Soil Science Society of American J, 45(4): 777-781.
Hao R, Wang G. (2003) Coreflood Experiment of Heavy Oil by Thermus SP3. J. Can. Petrol. Technol. 42(3): 36-39.
Hao R, Lu A, Zeng Y. (2004) Effect of crude oil by thermophilic bacterium. J. Petrol. Sci. Eng. 43(3-4): 247-258.
Hao R, Lu A, Wang G. (2004) Crude-oil-degrading thermophilic bacterium isolated from an oil field. Can. J. Microbiol. 50: 175-182.
Lea FM. (1970). The Chemistry of Cement and Concrete. Edward Arnold (Publishers) Ltd. (3rd edition), pp. 31, 121, 132, 416, 560, 621, 657.
McGovern-Traa et al. (1997) Petroleum Geology of the Irish Sea and Adjacent areas. Geological Society Special publication No. 124,229-236. Meadows NS, Trueblood SP, Hardman M, McGowan G (eds).
Omek D, Jayaraman A, Syrett BC, Hsu CH, Mansfeld FB, Wood TK. (2002) Pitting corrosion inhibition of aluminum 2024 by *Bacillus* biofilms secreting polyaspartate or gamma-polyglutamate. Appl Microbiol Biotechnol. 58(5): 651-657.
Saasen A, Salmelid B, Blomberg N, Hansen K, Young SP, Justnes H. The Use of Blast Furnace Slag in North Sea Cementing Applications. SPE28821, pp. 143-153, Proceedings, European Petroleum Conference, London, UK (Oct. 25-27, 1994).
Search Report issued on Oct. 26, 2009 for EA 200802357, which was filed on Jun. 17, 2005 (Applicant—Statoil ASA; Inventor—Kotlar et al).
Search Report issued Oct. 1, 2007 for GB 0712395.3, which was filed Jun. 26, 2007 (Applicant—Statoilhydro ASA; Inventor—H.K. Kotlar).
First Office Action issued Dec. 18, 2000 for CN 200680014248.7 (Applicant—Statoilhydro ASA; Inventor—Godoy et al.).
International Preliminary Report on Patentability issued Mar. 2, 2010 for PCT/GB2008/002912, which was filed on Aug. 29, 2008 and published as Mar. 5, 2009 on WO 2009/027680 (Applicant—Statoilhydro ASA; Inventors: Kotlar et al).
Written Opinion issued Feb. 28, 2008 for PCT/GB2008/002912, which was filed on Aug. 29, 2008 and published as Mar. 5, 2009 on WO 2009/027680 (Applicant—Statoilhydro ASA; Inventors: Kotlar et al).
International Search Report issued Dec. 8, 2008 for PCT/GB2008/002912, which was filed on Aug. 29, 2008 and published as Mar. 5, 2009 on WO 2009/027680 (Applicant—Statoilhydro ASA; Inventors: Kotlar et al).
International Preliminary Report on Patentability issued Oct. 30, 2007 for PCT/GB2006/001524, which was filed on Apr. 26, 2006 and published as WO 2006/114623 on Nov. 2, 2006 (Inventors—Godoy et al.; Applicant—Statoil ASA).
Written Opinion issued Oct. 26, 2007 for PCT/GB2006/001524, which was filed on Apr. 26, 2006 and published as WO 2006/114623 on Nov. 2, 2006 (Inventors—Godoy et al.; Applicant—Statoil ASA).
International Search Report issued Oct. 13, 2006 for PCT/GB2006/001524, which was filed on Apr. 26, 2006 and published as WO 2006/114623 on Nov. 2, 2006 (Inventors—Godoy et al.; Applicant—Statoil ASA).
Written Opinion issued Dec. 29, 2009 for PCT/GB2008/002209, which was filed on Jun. 26, 2008 and published as WO 2009/001098 on Dec. 31, 2008 (Inventor—H.K. Kotlar; Applicant—Statoil ASA).
International Preliminary Report on Patentability issued Jun. 24, 2009 for PCT/GB2008/002209, which was filed on Jun. 26, 2008 and published as WO 2009/001098 on Dec. 31, 2008 (Inventor—H.K. Kotlar; Applicant—Statoil ASA).
International Search Report issued Mar. 4, 2009 for PCT/GB2008/002209, which was filed on Jun. 26, 2008 and published as WO 2009/001098 on Dec. 31, 2008 (Inventor—H.K. Kotlar; Applicant—Statoil ASA).
International Preliminary Report on Patentability issued on Sep. 12, 2003 for PCT/GB02/023359, which was filed on May 21, 2002 and published as WO 02/095187 on Nov. 28, 2002 (Applicant—Statoil ASA; Inventor—Kotlar et al.).
International Search Report issued on Mar. 10, 2003 for PCT/GB02/023359, which was filed on May 21, 2002 and published as WO 02/095187 on Nov. 28, 2002 (Applicant—Statoil ASA; Inventor—Kotlar et al.).
Written Opinion issued on Nov. 16, 2004 for PCT/GB2005/02390, which was filed on Jun. 17, 2005 and published as WO 2005/124100 on Dec. 29, 2005 (Applicant—Statoil ASA; Inventor—Kotlar et al.).
International Preliminary Report on Patentability issued on May 30, 2006 for PCT/GB2005/02390, which was filed on Jun. 17, 2005 and published as WO 2005/124100 on Dec. 29, 2005 (Applicant—Statoil ASA; Inventor—Kotlar et al.).
International Search Report issued on Nov. 18, 2005 for PCT/GB2005/02390, which was filed on Jun. 17, 2005 and published as WO 2005/124100 on Dec. 29, 2005 (Applicant—Statoil ASA; Inventor—Kotlar et al.).
Written Opinion issued on Nov. 16, 2006 for PCT/GB2005/002385, which was filed on Jun. 17, 2005 and published as WO 2005/124099 on Dec. 29, 2005 (Applicant—Statoil ASA; Inventor—H.K. Kotlar).
International Preliminary Report on Patentability issued on Apr. 3, 2006 for PCT/GB2005/002385, which was filed on Jun. 17, 2005 and published as WO 2005/124099 on Dec. 29, 2005 (Applicant—Statoil ASA; Inventor—H.K. Kotlar).
International Search Report issued on Nov. 18, 2005 for PCT/GB2005/002385, which was filed on Jun. 17, 2005 and published as WO 2005/124099 on Dec. 29, 2005 (Applicant—Statoil ASA; Inventor—H.K. Kotlar).
Request for Continued Examination filed Jan. 26, 2012, in U.S. Appl. No. 11/919,367, filed Apr. 26, 2006 (Inventors: Godoy et al.).
Notice of Allowance issued on Mar. 2, 2012, in U.S. Appl. No. 11/919,367, filed Apr. 26, 2006 (Inventors: Godoy et al.).
Response to Final Office Action filed Mar. 19, 2012, in U.S. Appl. No. 11/629,729, filed Apr. 23, 2007 (Inventors: Kotlar et al.).
Request for Continued Examination filed Mar. 19, 2012, in U.S. Appl. No. 11/629,729, filed Apr. 23, 2007 (Inventors: Kotlar et al.).
"Expanding Heavy Oil Bitumen Resources while Mitigating GHG Emissions and Increasing Sustainability", Prepared by Petroleum Technology Alliance Canada (May 31, 2006).
Issue Notification issued on Jun. 13, 2012, in U.S. Appl. No. 11/919,367, filed Apr. 26, 2006 (Inventors: Godøy et al.).
Notice of Allowance issued on Oct. 26, 2011 for U.S. Appl. No. 11/919,367, filed Apr. 26, 2006 [Inventor—Godoy; Applicant—Statoil ASA; [3 pages].
Applicant Initiated Interview Summary issued on Feb. 22, 2012 for U.S. Appl. No. 11/629,729, filed Jun. 17, 2005 [Inventor—Kotlar; Applicant—Statoil ASA; [4 pages].
Final Office Action issued on Dec. 19, 2011 for U.S. Appl. No. 11/629,729, filed Jun. 17, 2005 [Inventor—Kotlar; Applicant—Statoil ASA; [9 pages].
Response to Non-Final Office Action filed on Dec. 9, 2011 for U.S. Appl. No. 11/629,729, filed Jun. 17, 2005 [Inventor—Kotlar; Applicant—Statoil ASA; [10 pages].

\* cited by examiner

METHOD OF ENHANCING OIL RECOVERY

CROSS-REFERENCE TO RELATED APPLICATIONS

The present application is a National Phase Application of International Application No. PCT/GB2008/002209, filed Jun. 26, 2008, which claims priority to Great Britain Patent Application No. 0712395.3 filed Jun. 26, 2007, and which applications are incorporated herein fully by this reference.

BACKGROUND OF THE INVENTION

1. Field of the Invention

This invention relates to a method of enhancing oil recovery from a subterranean hydrocarbon reservoir and to compositions for use in such methods.

2. Background

Hydrocarbons, i.e. gas and oils, are a limited resource and thus it is important to maximize the amount of oil that is recovered from underground reservoirs.

For certain reservoirs, particularly heavy oil reservoirs in which the oil contains large quantities of long chain hydrocarbons, paraffins, waxes, aromatics (including polyaromatic hydrocarbons—PAH), terpenoids, asphaltenes, etc., oil sand or shale reservoirs, and bitumen reservoirs the techniques currently used result in the recovery of less than 10% wt. of the oil in the reservoir. To a large extent this is because the oil is of such a high viscosity, or otherwise flows so poorly, that only limited quantities will reach the production wells.

One approach that has been adopted to this problem is to inject superheated steam down injection wells above the production wells, e.g. in substantially horizontal sections of the bore holes where the injection bore hole is above the production bore hole. The temperature increase resulting from superheated steam injection serves to reduce the viscosity of the heavy oil which then, under the influence of gravity, flows more readily into the production bore hole. This procedure has been referred to as steam-assisted gravity drainage (SAGD) or VAPEX.

A further approach to increasing hydrocarbon recovery is hot solvent extraction in which a heated organic solvent is injected into the matrix to reduce the viscosity of the hydrocarbon and improve its flow characteristics in the matrix. In this technique, injection may be into an injection bore hole (i.e. as with steam injection) or it may be into the production bore hole. Typically the hot solvent used is selected from naphtha, diesel, toluene, and other hydrocarbon fractions. The injection temperature will typically be in the range 20 to 400° C., especially 80 to 100° C.

Yet another extraction enhancement procedure is cold heavy oil production with sand (CHOPS) which involves sand influx into the production well. Another procedure is hydraulic fragmentation (fracking) of the matrix at the production well. Further examples of enhanced oil recovery techniques for heavy oil, oil sand or bitumen reservoirs include cyclic steam stimulation (CSS), and pulsed pressure flow enhancement. Down-hole generation of gases to increase down-hole pressure and hence oil flow into the production well may also involve direct contact steam generation and thermal oxidation processes (to generate $CO_2$ from combustion of hydrocarbons down-hole).

The techniques however are cumbersome, environmentally unfriendly and improvements and alternatives are desirable.

BRIEF SUMMARY OF THE INVENTION

In one aspect, the present disclosure provides a method of method of enhancing heavy oil recovery from a subterranean hydrocarbon reservoir, said method comprising injecting into said reservoir through a matrix injection section of a well a microorganism capable of digesting oil, and recovering oil from an oil receiving section of a production well, where said injection section is in said production well or is in an injection well and is above or adjacent said oil receiving section, and wherein microorganism injection is preceded by another oil extraction enhancing procedure.

DETAILED DESCRIPTION OF THE INVENTION

Figure 1:
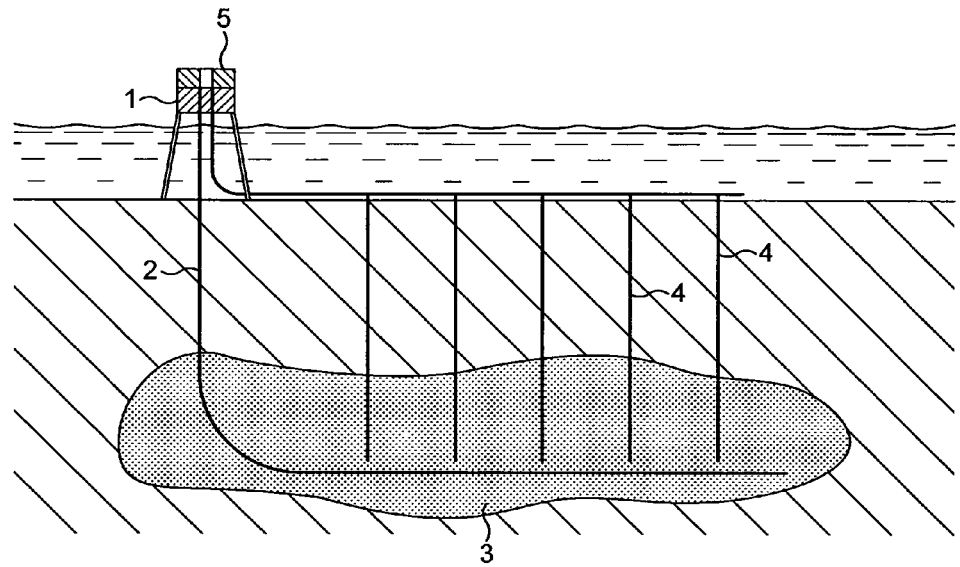
FIG. 1 is a schematic vertical section through a shallow heavy oil reservoir.

We have now realized that oil recovery may be enhanced if heavy oil-degrading microorganisms are introduced through an injection well into the formation above or adjacent a separate production well or into the formation at a production well, in conjunction with other oil recovery enhancement techniques such as steam injection, hot solvent extraction, CHOPS, fracking, CSS, etc., as described above.

Thus viewed from one aspect the invention provides a method of enhancing oil recovery from a subterranean hydrocarbon reservoir, especially a heavy oil reservoir, said method comprising injecting into said reservoir through a matrix injection section of a well a microorganism capable of digesting oil, and recovering oil from an oil receiving section of a production well, where said injection section is in said production well (e.g. at said oil receiving section) or is in an injection well and is above or adjacent said oil receiving section, and wherein microorganism injection is preceded by another oil extraction enhancing procedure (such as steam or hot solvent injection, CHOPS, hydraulic fragmentation, etc.), particularly preferably through the same injection section, e.g. 1 to 150 days beforehand Microorganism injection is especially preferably effected through a plurality of injection wells for the (or each) production well, e.g. 5 to 20 such injection wells, for example using an array of "slim" injection wells each terminating (i.e. with a matrix entry site) near a matrix exit site of the production well, i.e. multi-tracking injection wells. This is particularly desirable for shallow reservoirs, e.g. at a depth of 200 to 600 m subsurface. This is shown schematically in the accompanying Figure.

By oil degrading or oil digesting it is meant that the microorganism (or microorganism mixture) is capable of chemically modifying oil to reduce the viscosity or wax, asphaltene or aromatics content thereof whereby to cause it to flow more freely in the matrix (i.e. the rock from which the reservoir is formed). Such modification will generally involve fragmentation of one or more components of the oil (e.g. fragmentation of alkanes into smaller alkanes), ring opening in aromatic compounds, or opening or cleavage of other large organic compounds, for example asphaltenes. Desirably, the microorganisms cleave or fragment the oil components so as to render the oil viscosity sufficiently low as to enhance oil recovery. Thus it is preferred that the microorganism used not simply be one that generates a surfactant or a gas (e.g. methane), and particularly preferably a microorganism cocktail is used which causes ring opening, especially in combination with a microorganism that causes hydrocarbon chain shortening. Other factors remaining constant, production flow is approximately inversely proportional to the down-hole (heavy) oil viscosity and so degradation using the technique of the invention may enhance liquid hydrocarbon flow by a factor of from ten to hundreds of percent by volume.

Many microorganisms (generally eubacteria or archae) are known to digest oil and such microorganisms may be used in the method of the present invention if they are capable of surviving at the temperatures and pressures experienced down-hole. Typical examples include *Bacillus* sp., *Thermus* sp., *Pseudomonas* sp., *Geobacillus* sp., *Arthrobacter* sp., *Sphingomonas* sp., *Mycobacterium* sp., *Burholderia* sp., *Acinebacter* sp., *Thermovirga* sp., *Archaeoglobus* sp., *Thermosipho* sp., *Symbiobacterium* sp., *Methanosaeta* sp., *Epsilonproteobacterium* sp., *Syntrophus* sp., *Nocardioides* sp., *Deferribacter* sp., *Chloraflexi* sp., etc.

Preferably however the inoculate, the microorganism composition injected in accordance with the present invention, will contain at least 2 and preferably at least 3 different microorganism species, in particular at least one capable of chain-shortening alkanes and at least one capable of ring opening aromatics. Examples of microorganisms capable of chain-shortening alkanes include *Bacillus* sp., *Geobacillus* sp., *Acinebacter* sp., *Methanosaeta* sp. and in particular *Acinebacter venetianus, Bacillus thermoleovorans, Bacillus aeolis* and *Geobacillus thermodenitrificans* while examples of microorganisms capable of degrading aromatics include *Nocardioides* sp., *Geobacillus* sp., and *Syntrophus* sp., eg *Geobacillus subterraneous*. Use of *Thermus* sp. will result in decrease of aromatics, resins and asphaltenes and reduced viscosity, eg *Thermus* strains SP3, C2 and TH-2 (see Hao et al. J. Can. Petrol. Tecnol. 43:36-39 (2003), Can. J. Microbiol. 50:175-182(2004), and J. Petrol. Sci. Eng. 43:247-258 (2004)). Use of *Pseudomonas* sp. will result in n-alkane and PAH degradation and reduced viscosity, eg *Pseudomonas aeruginosa*. Moreover, *Thermus brockii* is capable of degrading hexadecane and pyrenes (see Geitkenhauer et al., Water Sci Technol 47: 123-130(2003)).

Rather than producing a microorganism inoculation composition by mixing (top-side or on site) individual microorganisms, it is possible and indeed preferable to use microorganism cocktails from or developed from naturally occurring microorganism communities, e.g. microorganism communities from subterranean hydrocarbon reservoirs, from oil shales, bitumen sources, or, especially from mud volcanoes. Likewise appropriate microorganisms may of course be produced by mutagenesis or by genetic engineering.

It is especially preferred that the inoculate contain microorganisms selected from the species *Bacillus thermoleovorans Thermus brockii, Syntrophus aciditrophicus, Acinebacter venetianus, Deferribacter desulfuricans, Thermosipho geolei, Thermosipho africanus, Symbiobacterium thermophilium, Thermovirga lienii, Sphingomonas stygia, Sphingomonas aromaticivorans, Sphingomonas subterranean, Sphingomonas yanoikuyae, Pseudomonas putida, Burholderia* sp. and *Archaeoglobus fulgidus*. Particular deposited strains that can be used include *Bacillus thermoleovorans* AB034902 (Genbank), *Bacillus aeolis* AY603079 (Genbank), *Pseudomonas aeruginosa* AM087130 (Genbank), *Geobacillus thermodenitrificans* DQ243788 (Genbank), *Geobacillus subterraneous* DQ355385 (Genbank), *Sphingomonas stygia* DSMZ12445, *Sphingomonas* sp DSMZ 7526, *Sphingomonas* sp DSMZ 11094, *Sphingomonas aromaticivorans* DSMZ 12444, *Sphingomonas subterranean* DSMZ 12447, *Sphingomonas yanoikuyae* DSMZ 6900, *Pseudomonas putida* NCIMB 9815, *Pseudomonas putida* NCIMB 9816, *Pseudomonas putida* NCIMB 10015, *Methanosaeta* sp. AJ 133791, *Epsilonproteobacteria* AY 570641, *Syntrophus aciditrophicus* CP 000252, *Nocardioides* sp. D 87974, *Deferribacter desulfuricans* AB 086060, *Chlorflexi* sp. AB 074961, *Thermovirga lienii* DQ 071273, *Archaeoglobus fulgidus* DQ 131905, *Thermosipho geolei* AJ 272022, *Acinebacter venetianus* ATCC 31012 and *Symbiobacterium* sp. AB 052392. It is particularly preferred that it contain microorganisms of at least the species *Sphingomonas* sp., *Pseudomonas* sp., *Burholderia* sp., *Thermovirga lienii, Archaeoglobus fulgidus, Acinebacter venetianus, Thermosipho geolii* and *Symbiobacterium* sp. Such mixtures are new and form a further aspect of the invention. Viewed from this aspect, the invention provides a microorganism mixture for hydrocarbon reservoir treatment, said mixture comprising microorganisms of at least two, preferably at least three, of the following species: *Sphingomonas* sp., *Pseudomonas* sp., *Burholderia* sp., *Thermovirga lienii, Archaeoglobus fulgidus, Acinebacter venetianus, Thermosipho geolii* and *Symbiobacterium* sp, in particular a said mixture further comprising vitamins and minerals and preferably a mixture in liquid or dry powder form, and preferably alkane-free, eg isolated from any matrix or hydrocarbon in which it may occur naturally.

In particular, a combination of *Sphingomonas* sp., *Pseudomonas* sp., and *Burholderia* sp. may be used, eg *Sphingomonas stygia, Sphingomonas aromaticivorans, Sphingomonas subterranean, Sphingomonas yanoikuyae, Pseudomonas putida*, and *Burholderia* sp., especially *Sphingomonas stygia* DSMZ12445, *Sphingomonas* sp DSMZ 7526, *Sphingomonas* sp DSMZ 11094, *Sphingomonas aromaticivorans* DSMZ 12444, *Sphingomonas subterranean* DSMZ 12447, *Sphingomonas yanoikuyae* DSMZ 6900, *Pseudomonas putida* NCIMB 9815, *Pseudomonas putida* NCIMB 9816, *Pseudomonas putida* NCIMB 10015, and *Burholderia* sp.

For shallow oil fields it may be adequate to use in the inoculate microorganisms that grow at atmospheric pressure, however for deeper fields it is important that the microorganism be both thermophiles and piezophiles.

Selecting appropriate combinations of microorganisms for use in shallow fields is thus relatively simple. A candidate microorganism or microorganism cocktail may be incubated with a sample of heavy oil, preferably from the site to be treated, and if a reduction in viscosity is achieved the candidate may proceed. For deeper fields the incubation is preferably effected at the down hole temperatures and/or pressures of the site to be treated. In both cases, the ability to withstand temperatures of 60 to 120° C., especially 70 to 100° C. is preferred as such microorganisms may readily be injected into sites where steam or hot solvent injection has been, is being or is to be effected: otherwise a significant delay between steam or hot solvent injection and microorganism injection may be required.

Where steam or hot solvent injection is to be used in the method of the invention, the timing of the microorganism injection should be such that the microorganisms are not injected into an environment in which the temperature is lethal. The delay time for microorganism injection may readily be calculated from the heat dissipation characteristic of the matrix.

Screening of a microorganism cocktail is preferably done repeatedly, with an aliquot of the culture at the end of one digestion period then being presented with a fresh heavy oil sample to digest. This is important as degradation may require the contribution of one microorganism species after that of another and it may thus be necessary that, down hole, all of the necessary species continue to grow. Where, after several digestions, the microorganism population is stable, the candidate may be developed further.

Before down hole injection, the microorganism inoculate is preferably mixed with oil to prime its enzyme systems.

Down hole injection of the microorganism may if desired be preceded by, accompanied by or followed by down hole injection of nutrients for microorganism growth, e.g. minerals and amino acids, or oil digesting enzymes. The injection of further carbon sources, eg ones such as acetate which are water-soluble, is particularly preferred.

Down hole injection of the microorganism may if desired be preceded by fracturing of the matrix around the injection site, e.g. to provide a reservoir for microorganism growth.

Down hole injection of the microorganism into an injection well is preferably effected in conjunction with steam or superheated water or organic solvent injection down the same injection well, e.g. at an injection temperature of 100-400° C. This injection may precede microorganism injection (where the steam or solvent injection temperature is lethal to the microorganisms) or may occur simultaneously; however it is preferred that the enhanced oil recovery technique, steam or hot solvent injection, be effected before microorganism injection, e.g. a period of up to 1 year, for example 1 to 150 days, preferably 5 to 20 days, beforehand. Particularly desirably, the enhanced oil recovery technique (eg steam or hot solvent injection) and microorganism injection are effected repeatedly, in particular in specifically designed sequenced procedures.

Down hole injection of the microorganism into a production well is preferably effected in conjunction with the enhanced oil recovery technique, e.g. CHOPS, hot organic solvent injection, hydraulic fragmentation, etc.; this may precede microorganism injection or be performed simultaneously or later. In the case of hot solvent injection, solvent injection is preferably effected beforehand with a sufficient time delay that the matrix temperature is tolerable to the microorganisms when they are injected, e.g. a delay of up to 1 year, for example 1 to 150 days, especially 5 to 20 days. Such treatments of a production well are preferably repeated.

Particularly preferably, microorganisms are injected into both injection and production wells, in each case preferably in conjunction with a further hydrocarbon extraction enhancing technique (i.e. SAG-D, CHOPS, etc).

If desired the microorganism inoculate may include microorganisms which generate gas and/or acid and hence degrade the matrix.

The method of the invention can serve to reduce the usage or aggressiveness of the other hydrocarbon extraction enhancing techniques, such as SAG-D and so reduce their environmental impact.

The invention is especially applicable to hydrocarbon reservoirs which yield heavy oils, e.g. from medium crude (31-22 API) to heavy crude (22-10 API) to extra heavy crude (<10 API) oils, and the microorganism treatment, particularly with thermophilic and/or piezophilic microorganisms, is preferably in conjunction with, e.g. simultaneously or sequentially, at least one of SAG-D, CHOPS, VAPEX, hot solvent extraction and hot water extraction.

Figure 2:
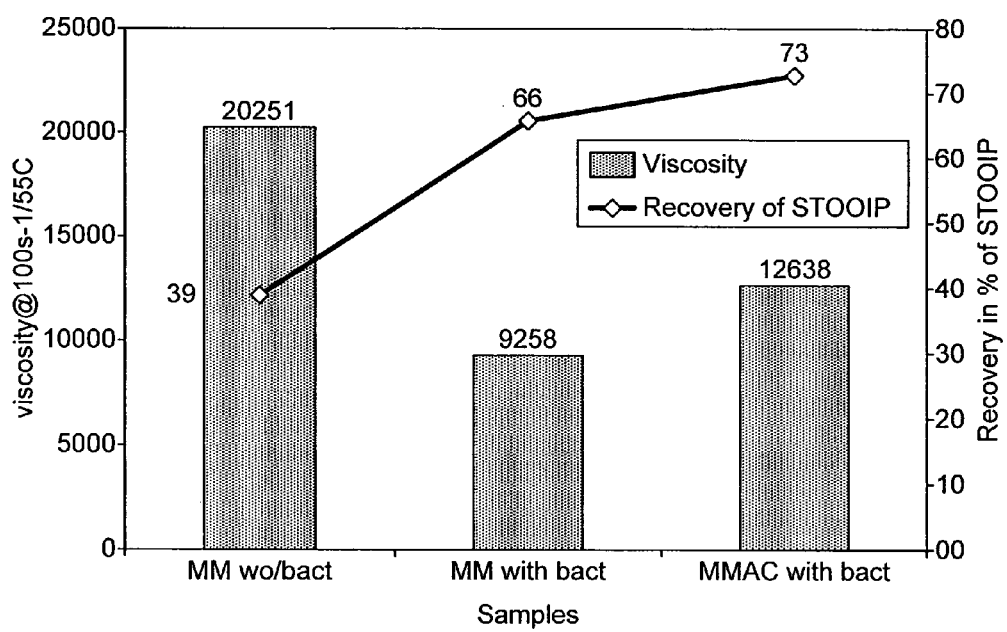
FIG. 2 is a chart of oil recovery and oil viscosity without and with treatment according to the invention.

The invention will now be illustrated by the following non-limiting Examples and the accompanying drawings, in which:

FIG. 1 is a schematic vertical section through a shallow heavy oil reservoir;

and FIG. 2 is a chart of oil recovery and oil viscosity without and with treatment according to the invention.

Referring to FIG. 1 there is shown an offshore platform 1 having a producer well 2 extending into a shallow heavy oil reservoir 3. From platform 1 a series of slim injector wells 4 are fed by injection unit 5 which serves to inject steam and microorganism culture sequentially.

Example 1

Treatment of Zuata Crude Oil with Microorganisms Endogenous to Argentine Bitumen Materials:

Bitumen (from Argentina)

Treatment medium 1 (TMS1) content per liter: 5 g $FeSO_4.7H_2O$, 0.29 g $CuSO_4.5H_2O$, 0.44 g $ZnSO_4.7H_2O$, 0.15 g $MnSO_4.H_2O$, 0.01 g $Na_2MoO_4.2H_2O$, 0.02 g $CoCl_2.6H_2O$, 50 ml conc HCl.

Treatment medium 3 (TMS3) content per liter: 2021.2 mg $Na_2SiO_3.9H_2O$, 445.5 mg NaF, 5651.7 mg $K_2B_4O_7.4H_2O$, 47.9 mg $NaIO_3$, 180.7 mg $KAl(SO_4)_2.12H_2O$, $SnCl_2.2H_2O$.

Treatment medium 4 (TMS4) content per liter: 346.8 mg $NiCl_2.6H_2O$, 101.4 mg $Na_2SeO_3.5H_2O$, 18 mg $V_2O_5$, 14 mg $K_2Cr_2O_7$, 3.6 mg $Na_2WO_4.2H_2O$.

Vitamin stock solution (VSS) content per liter: 2.00 g biotin, 2.00 g folic acid, 10.00 g pyridoxine-HCl, 5.00 g thiamine-HCl.$2H_2O$, 5.00 g riboflavin, 5.00 g nicotinic acid, 5.00 g D-Ca-pantothenate, 0.10 g vitamin B12, 5.00 g p-aminobenzoic acid, 5.00 g lipoic acid.

Mineral medium (MM) content per liter: 0.9 g $NH_4NO_3$, 0.05 g $CaCl_2.2H_2O$, 0.2 g $MgSO_4.7H_2O$, 3.06 g $Na_2HPO_4.2H_2O$, 1.52 g $KH_2PO_4$, 1 ml TMS1, 1 ml TMS3, 1 ml TMS4, 1 ml VSS. pH adjusted to pH 7.0.

Process medium 1 (PM1): Zuata crude oil (from Venezuela) 0.4% (w/vol) in MM

Process medium 2 (PM2): Zuata crude oil 1.6% (w/vol) in Light Gas Oil (LGO), 1% (vol/vol) in MM Inoculation:

Bitumen samples (0.5 g) were inoculated into shakeflasks (Bellco, 250 ml) containing 50 ml PM1 or PM2.

Cultivation:

The shake flasks were incubated at 50° C. on a rotary shaker at 200 rpm and 90% humidity (Infors Multitron incubator) for 34 days.

Example 2

Treatment of Zuata Heavy Oil with Microorganisms Endogenous to a Mud Volcano

Materials:

Mud from Mud Volcano

Widdel Basal Salt Media B (WBSB) content per liter: 30.0 g NaCl, 0.15 g $CaCl_2.2H_2O$, 3.0 g $MgCl_2.6H_2O$, 0.9 g $NH_4NO_3$, 0.5 g KCl, 0.18 g $Na_2SO_4$, 3.06 g $Na_2HPO_4.2H_2O$, 1.52 g $KH_2PO_4$, 1 ml TMS1, 1 ml TMS3, 1 ml TMS4, 1 ml VSS. pH adjusted to 8.2.

Process medium 3 (PM3): Zuata crude oil dissolved 10% (w/vol) in heptamethyl nonane (HMN—an inert solute) added 5% (vol/vol) to WBSB Inoculation:

Mud samples (0.5 ml) were inoculated into shakeflasks (Bellco, 250 ml) containing 50 ml PM3.

Cultivation:

The shake flasks were incubated at 50° C. on a rotary shaker at 200 rpm and 90% humidity (Infors Multitron incubator) for 28 days.

Example 3

Treatment of Linerle Crude Oil with Microorganism Cocktail

Materials:

Microorganism cocktail (MC): A mixture of the following strains: *Pseudomonas putida* NCIMB 9815, NCIMB 9816 and NCIMB 10015 and *Burkholderia* sp isolates from biosludge from a refinery water treatment plant. The microorganisms were cultivated in inoculum medium (IM) for up to 24 hours and harvested by centrifugation (10 min, 5 000×g). The cell-pellets were washed twice with MM medium (20 ml) and the pellet resuspended in MM medium (500 µl). The microorganism cocktail (MC) was prepared by mixing the washed and resuspended microorganisms in equal concentrations.

Inoculum medium (IM) per liter: 20.0 g yeast extract, 1.0 g $MgSO_4.7H_2O$, 5 g NaCl, pH adjusted to 7.5.

Process medium 4 (PM4): 5% (vol/vol) heat-treated Linerle crude oil (from the Norwegian continental shelf, heated to 60° C. for 2 hours) was added to MM.

Process medium 4 with yeast extract (PM4-YE): 5% (vol/vol) heat-treated Linerle crude oil (from the Norwegian continental shelf, heated to 60° C. for 2 hours) was added to MM containing 0.1 g yeast extract.

Inoculation:

The MC was inoculation into shakeflasks (Bellco, 250 ml) containing 50 ml PM4 or 50 ml PM4-YE to a final $OD_{660}=1.0$.

Cultivation:

The shake flasks were incubated at 30° C. on a rotary shaker at 200 rpm (Infors Multitron incubator) for 9 days.

Example 4

Treatment of Zuata Heavy Oil in Sand with Microorganisms from Sediment

Materials:

Microorganism inoculum (MI): A mixed inoculum of microorganisms isolated from sediment samples Sand column: Zuata crude oil mixed in a 9:36 weight ratio with barskarp sand, packed into glass columns (Omnifit).

Inoculation:

MI (5 ml, approx $10^9$ cells/nil) was added to the sand column after water flooding the column for 4 days.

Cultivation:

After inoculation, the sand columns were shut-in for 24 hours prior to circulation of MM was initiated. MM was circulated at a rate of 171 ml/hour.

The results of this treatment of heavy oil in reservoir-like conditions is shown in FIG. 2 of the attached drawings. FIG. 2 shows the oil recovery from sand packs as a percentage of standard total original in place (STOOIP—right hand ordinate and plot) and the viscosity in mPa·s of the treated oil at a shear rate of 100 $s^{-1}$ and 55° C. (left hand ordinate and bar chart). The left hand values are for Zuata heavy oil without treatment. The centre values are for Zuata heavy oil treated under the conditions specified in this Example. The right hand values are for Zuata heavy oil treated under the conditions specified in this Example, but with the addition of 5 g/L acetate (eg sodium acetate) to the MM.

Example 5

Viscosity Effect on Crude Oils

The viscosity of treated and untreated heavy crude oil type 1 was determined at 30° C. at a shear of up to 1000 $s^{-1}$. While untreated gave a viscosity value of 417 mPas, for the treated sample this was reduced to 130 mPas. In a further test using Zuata crude oil, treated and untreated, in a radial reservoir model, at 60° C. and a shear rate of up to 700 $s^{-1}$, a significant reduction in viscosity was noted at all shear rates which became increasingly prominent at shear rates above 100 $s^{-1}$.

What is claimed is:

1. A method of enhancing heavy oil recovery from a subterranean hydrocarbon reservoir, said method comprising injecting into said reservoir through a matrix injection section of a well a microorganism capable of digesting heavy oil, and recovering heavy oil from an oil receiving section of a production well, wherein said injection section is in said production well or is in an injection well and is above or adjacent said oil receiving section, wherein microorganism injection is preceded by another heavy oil extraction enhancing procedure, and wherein said another heavy oil enhancing procedure and said microorganism injection are effected repeatedly.

2. A method as claimed in claim 1, wherein microorganism injection is into an injection well.

3. A method as claimed in claim 2, wherein steam, superheated water or organic solvent is also injected through said injection well.

4. A method as claimed in claim 1, wherein microorganism injection is into a production well.

5. A method as claimed in claim 4, wherein organic solvent is also injected through said production well.

6. A method as claimed in claim 1, wherein said microorganism is an alkane chain-shortening microorganism.

7. A method as claimed in claim 1, wherein said microorganism is an aromatic ring opening microorganism.

8. A method as claimed in claim 1, comprising injecting said microorganism into said reservoir at a plurality of sites, each above or adjacent a said oil receiving section of a said production well.

9. A method as claimed in claim 1, wherein the heavy oil has an API of 22 or less.

10. A method as claimed in claim 1, wherein the heavy oil has an API of less than 10.

11. A method as claimed in claim 1, wherein the another oil extraction enhancing procedure is selected from steam-assisted gravity drainage (SAGD), VAPEX, hot solvent extraction, cold heavy oil production with sand (CHOPS), fracking, cyclic steam stimulation (CCS), steam injection, hot water extraction, and pulsed pressure flow enhancement.

12. A method as claimed in claim 1, wherein the another oil extraction enhancing procedure is selected from VAPEX, hot solvent extraction, CHOPS, fracking, hot water extraction, and pulsed pressure flow enhancement.

13. A method as claimed in claim 1, wherein said microorganism is from a microorganism community from subterranean reservoirs, from oil shales, bitumen sources, or mud volcanoes.

14. A method as claimed in claim 1, wherein said microorganism is able to withstand temperatures of 60° C. to 120° C.

15. A method as claimed in claim 14, wherein said microorganism is able to withstand temperatures of 70° C. to 100° C.

16. A method as claimed in claim 1, wherein said microorganism is selected from the group consisting of *Bacillus* sp., *Thermus* sp., *Pseudomonas* sp., *Geobacillus* sp., *Arthrobacter* sp., *Sphingomonas* sp., *Mycobacterium* sp., *Burholderia* sp., *Acinebacter* sp., *Thermovigra* sp., *Archaeoglobus* sp., *Thermosipho* sp., *Symbiobacterium* sp., *Methanosaeta* sp., *Epsilonproteobacerium* sp., *Syntrophus* sp., *Nocardioides* sp., *Deferribacter* sp., and *Chloraflexi* sp.

17. A method as claimed in claim 16, wherein said microorganism is a mixture of at least two microorganisms of the following species: *Sphingomonas* sp., *Pseudomonas* sp., *Burholderia* sp., *Thermovigra lienii, Archaeoglubus fulgidus, Acinebacter venetianus, Thermosipho geolii*, and *Symbiobacterium* sp.

18. A method as claimed in claim 17, comprising microorganisms of the species *Sphingominas* sp., *Pseudomonas* sp., and *Burholderia* sp.

19. A method as claimed in claim 18, comprising microorganisms of the species *Sphingomonas stygia, Sphingomonas aromaticivorans, Sphingomonas subterranean, Sphingomonas yanoikuyae, Pseudomonas putida*, and *Burholderia* sp.

20. A method of enhancing heavy oil recovery from a subterranean hydrocarbon reservoir, said method comprising injecting into said reservoir through a matrix injection section of a well, a microorganism capable of digesting heavy oil, and recovering heavy oil from an oil receiving section of a production well, where said injection section is in said production well or is in an injection well and is above or adjacent said oil receiving section, and wherein microorganism injection is preceded by, or performed simultaneously with another heavy oil extraction enhancing procedure selected from the group consisting of SAGD, VAPEX, hot solvent extraction, CHOPS, fracking, CCS, steam injection, hot water extraction, and pulsed pressure flow enhancement wherein said another heavy oil extraction enhancing procedure and said microorganism injection are effected repeatedly.

21. A method as claimed in claim 20, wherein said another heavy oil extraction enhancing procedure is selected from the group consisting of VAPEX, hot solvent extraction, CHOPS, fracking, hot water extraction, and pulsed pressure flow enhancement.

22. A method as claimed in claim 20, wherein said another heavy oil extraction enhancing procedure is selected from the group consisting of SAGD, VAPEX, hot solvent extraction, CHOPS, fracking, CCS, steam injection, and hot water extraction.

23. A method as claimed in claim 20, wherein said microorganism is an alkane-chain shortening microorganism.

24. A method as claimed in claim 20, wherein said microorganism is an aromatic ring opening microorganism.

25. A method as claimed in claim 24, wherein said microorganism is a mixture of at least two microorganisms of the following species: *Sphingomonas* sp., *Pseudomonas* sp., *Burholderia* sp., *Thermovigra lienii, Archaeoglubus fulgidus, Acinebacter venetianus, Thermosipho geolii*, and *Symbiobacterium* sp.

26. A method as claimed in claim 25, comprising microorganisms of the species *Sphingomonas stygia, Sphingomonas aromaticivorans, Sphingomonas subterranean, Sphingomonas yanoikuyae, Pseudomonas putida*, and *Burholderia* sp.

27. A method as claimed in claim 20, wherein said microorganism is selected from the group consisting of *Bacillus* sp., *Thermus* sp., *Pseudomonas* sp., *Geobacillus* sp., *Arthrobacter* sp., *Sphingomonas* sp., *Mycobacterium* sp., *Burholderia* sp., *Acinebacter* sp., *Thermovigra* sp., *Archaeoglobus* sp., *Thermosipho* sp., *Symbiobacterium* sp., *Methanosaeta* sp., *Epsilonproteobacerium* sp., *Syntrophus* sp., *Nocardioides* sp., *Deferribacter* sp., and *Chloraflexi* sp.

28. A method as claimed in claim 27, comprising microorganisms of the species *Sphingomonas* sp., *Pseudomonas* sp., and *Burholderia* sp.

* * * * *